(12) United States Patent
Nishimi et al.

(10) Patent No.: US 7,674,633 B2
(45) Date of Patent: Mar. 9, 2010

(54) BIOSENSOR

(75) Inventors: Taisei Nishimi, Kanagawa (JP); Toshihide Ezoe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 677 days.

(21) Appl. No.: 11/524,303

(22) Filed: Sep. 21, 2006

(65) Prior Publication Data
US 2007/0071642 A1 Mar. 29, 2007

(30) Foreign Application Priority Data
Sep. 26, 2005 (JP) .............................. 2005-277340

(51) Int. Cl.
*G01N 33/553* (2006.01)
(52) U.S. Cl. ........................ 436/525; 436/501; 436/518; 422/58; 435/6
(58) Field of Classification Search .................. 422/58; 435/6; 436/501, 518, 525
See application file for complete search history.

(56) References Cited

U.S. PATENT DOCUMENTS

2003/0119054 A1* 6/2003 Mrksich et al. .............. 435/7.1
2003/0219753 A1* 11/2003 Quinn et al. .................... 435/6

* cited by examiner

*Primary Examiner*—Michael A Marcheschi
*Assistant Examiner*—Jonathan M Hurst
(74) *Attorney, Agent, or Firm*—Sughrue Mion, PLLC

(57) ABSTRACT

It is an object of the present invention to provide a technique of conserving a functional group used for binding a physiologically active substance in the form of an inactive ester, and converting it to an activated ester by simple operations immediately before formation of an amide bond. The present invention provides a biosensor which comprises a substrate that has been modified with a phenyl ester group having a substituent whose electron-withdrawing ability is increased as a result of a chemical reaction.

11 Claims, No Drawings

BIOSENSOR

TECHNICAL FIELD

The present invention relates to a biosensor, and a method of analyzing interaction among biomolecules using the above biosensor. In particular, the present invention relates to a biosensor used for surface plasmon resonance biosensors, and a method of analyzing interaction among biomolecules using the above biosensor.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The QCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

In all of the above-described techniques, the surface where a physiologically active substance is immobilized is important. Surface plasmon resonance (SPR), which is most commonly used in this technical field, will be described below as an example.

A commonly used measurement chip comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules.

As a thin film having a functional group capable of immobilizing a physiologically active substance, there has been reported a measurement chip where a physiologically active substance is immobilized by using a functional group binding to metal, a linker with a chain length of 10 or more atoms, and a compound having a functional group capable of binding to the physiologically active substance (Japanese Patent No. 2815120). Moreover, a measurement chip comprising a metal film and a plasma-polymerized film formed on the metal film has been reported (Japanese Patent Laid-Open (Kokai) No. 9-264843).

When a physiologically active substance having an amino group is allowed to bind to the surface of a biosensor having carboxylic acid, in general, the carboxylic acid existing on the biosensor surface is activated with 1-(3-dimethylaminopropyl)-3 ethylcarbodiimide (EDC) (which is a water-soluble carbodiimide) and N-hydroxysuccinimide (NHS) in an aqueous medium, and the biosensor surface is then allowed to react with the amino group of the physiologically active substance, so as to form a carboxylic amide. Even when a biosensor surface such as those used in surface plasmon resonance analysis (SPR) or quartz crystal microbalance (QCM) is produced, it has been reported that an amide bond is formed in water by the combination of EDC with NHS (JP Patent Laid-Open (Kokai) Nos. 11-281569 and 2000-39401).

However, when EDC is mixed with NHS in water, there has been a problem that "the stability of the obtained active ester is not sufficient and that it is hydrolyzed over time."

DISCLOSURE OF INVENTION

It is an object of the present invention to solve the aforementioned problems of the prior art techniques. That is to say, it is an object of the present invention to provide a technique of conserving a functional group used for binding a physiologically active substance in the form of an inactive ester, and converting it to an activated ester by simple operations immediately before formation of an amide bond.

As a result of intensive studies directed towards achieving the aforementioned object, the present inventors have found that the aforementioned object can be achieved by preparing a substrate that has been modified with a phenyl ester group having a substituent whose electron-withdrawing ability is increased as a result of a chemical reaction, and activating the above-described phenyl ester group via a chemical reaction immediately before allowing it to react with and bind to a compound having an amino group, thereby completing the present invention.

That is to say, the present invention provides a biosensor which comprises a substrate that has been modified with a phenyl ester group having a substituent whose electron-withdrawing ability is increased as a result of a chemical reaction.

Preferably, the substituent whose electron-withdrawing ability is increased as a result of a chemical reaction is a dialkylamino group.

Preferably, the substrate is a metal surface or a metal film which consists of a free electron metal selected from the group consisting of gold, silver, copper, platinum, and aluminum.

Preferably, the biosensor of the present invention is used in non-electrochemical detection, and more preferably is used in surface plasmon resonance analysis.

In another aspect, the present invention provides a method for immobilizing a compound having an amino group on a substrate, which comprises: activating a phenyl ester group existing on the substrate, which has a substituent whose electron-withdrawing ability is increased as a result of a chemical reaction, by a chemical reaction; and then allowing the activated phenyl ester group to react with the compound having an amino group.

Preferably, the substituent whose electron-withdrawing ability is increased as a result of a chemical reaction is a dialkylamino group.

Preferably, the chemical reaction is an alkylation reaction, a complexation reaction, or a diazotization reaction.

Preferably, the compound having an amino group is a physiologically active substance.

In a further aspect, the present invention provides the aforementioned biosensor of the present invention, on which a compound having an amino group is immobilized by the aforementioned method of the present invention.

In a further aspect, the present invention provides a method for detecting or measuring a substance interacting with a physiologically active substance, which comprises a step of allowing the biosensor of the present invention, to which a compound having an amino group binds, to come into contact with a test substance.

Preferably, a substance interacting with the compound having an amino group can be detected or measured by a non-electrochemical method, and more preferably, it can be detected or measured by surface plasmon resonance analysis.

BEST MODE FOR CARRYING OUT THE INVENTION

The embodiments of the present invention will be described below.

The biosensor of the present invention comprises a substrate that has been modified with a phenyl ester group having a substituent whose electron-withdrawing ability is increased as a result of a chemical reaction.

An active ester-forming compound, which is used to form an amide, has great electron-withdrawing ability. It has generally been known that an amide bond is formed by the nucleophilic attack of an amine component on a carbonyl carbon that has been activated by an electron-withdrawing group. Accordingly, in order to obtain both conservation stability and amide bond activity, a functional group is conserved in the form of an ester having low electron-withdrawing ability, and it is then converted to a compound having high electron-withdrawing ability by external stimulus immediately before formation of an amide bond. As a result, it is anticipated that both conservation stability and amide bond activity can be obtained. As a result of intensive studies based on such thoughts, the present invention has been completed.

The electron-withdrawing ability and electron-donating ability of the substituent of a substituted phenyl ester can be quantitatively evaluated by Hammett's substituent constant σ. The σ value is a value defined by Hammett et al, which is used to quantify the effects of the meta- and para-substituents of a benzene ring. The positive σ value indicates electron-withdrawing ability, and the negative σ value indicates electron-donating ability. The greater the absolute value, the greater the electron-withdrawing ability or electron-donating ability that can be obtained. The physical meanings of the Hammett's σ value and the calculation method thereof are described in detail in Naoki Inamoto, "*Hammett Soku* (Hammett Measurement)," Maruzen (1983); Okuyama Kaku, Hiroshi Yamataka, "*Yuki Hanno Ron* (Theory of Organic Reaction)," Asakura Shoten (2005); C. Hansch, A. Leo, R. W. Taft, *Chem. Rev.*, 91, 165-195 (1991), etc.

When the σ value of substituent X is defined as σ(X) and the σ value of substituent Y is defined as σ(Y) in the following formula 1, electron-withdrawing ability increased by external stimulus means σ(Y)−σ(X)>0. As the difference is great, the degree of the increased electron-withdrawing ability is also great. From the viewpoint of achievement of both conservation stability and reactivity, it is desired that the difference of electron-withdrawing ability based on the external stimulus be great. Thus, it is preferably σ(Y)−σ(X)>0.5, more preferably σ(Y)−σ(X)>0.8, and further more preferably σ(Y)−σ(X)>1.0.

The σ value of p-nitrophenol used in peptide synthesis is 0.78. Thus, it is assumed that σ value of approximately 0.70 or greater is effective for formation of an active ester. Accordingly, in the present invention, σ(Y)>0.70 is preferable, σ(Y)>0.80 is more preferable, and σ(Y)>0.85 is further more preferable.

Specific examples of the combination of substituents X with Y that satisfies two conditions may include the combinations shown in Table 1. In the table, $\sigma_m(X)$ and $\sigma_p(X)$ indicate the σ values obtained when X is substituted for meta- and para-positions, respectively. $\sigma_m(Y)$ and $\sigma_p(Y)$ indicate the σ values obtained when Y is substituted for meta- and para-positions, respectively. These values are cited from the aforementioned publication reported by Taft et al.

TABLE 1

Formula 1

R—C(=O)—O—C$_6$H$_4$—X  →(Stimulus)  R—C(=O)—O—C$_6$H$_4$—Y

| | X | Y | Stimulus | $\sigma_m(X)$, $\sigma_p(X)$ | $\sigma_m(Y)$, $\sigma_p(Y)$ |
|---|---|---|---|---|---|
| 1 | —N(CH$_3$)$_2$ | —N$^+$(CH$_3$)$_3$ | Methylation | −0.16, −0.83 | 0.88, 0.82 |
| 2 | —S(CH$_3$) | —S$^+$(CH$_3$)$_2$ | Methylation | 0.15, 0.00 | 1.00, 0.90 |
| 3 | —P(CH$_3$)$_2$ | —P$^+$(CH$_3$)$_3$ | Methylation | 0.03, 0.06 | 0.74, 0.73 |
| 4 | —P(Ph)$_2$ | —P(Ph)$_2$BF$_3$ | Complexation | 0.11, 0.19 | 0.67, 0.72 |
| 5 | —NH$_2$ | —N$_2$$^+$X$^−$ | Diazotization | −0.16, −0.66 | 1.76, 1.91 |

From the viewpoint of the difference in electron-withdrawing ability before and after the reaction and the availability of raw materials, the alkylation reaction of an (m-dimethylamino)phenyl ester is most preferable.

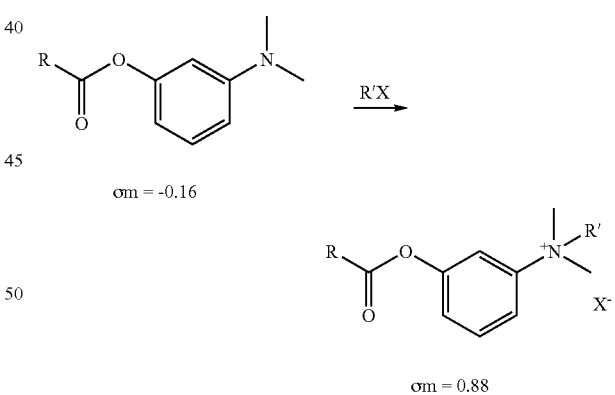

σm = −0.16

σm = 0.88

As an alkylating agent, known compounds such as dialkyl sulfate, alkylsulfonic acid, a benzyl halide, an alkyl halide, chlorine-containing lactam, heterocyclic sulfate, lactone, or carbonate ester can be used. Specific examples of such an alkylating agent used herein may include: dialkyl sulfates such as dimethyl sulfate, diethyl sulfate, or methyl sulfate; alkylsulfonic acids such as methylsulfonic acid or ethylsulfonic acid; benzyl halides such as benzyl chloride, benzyl bromide, or benzyl iodide; alkyl halides such as methyl chloride, ethyl bromide, ethyl chloride, octyl chloride, or stearyl chloride; chlorine-containing lactams such as N-chlormethylpyrrolidone or N-chlorethyl caprolactam; heterocyclic sulfates such as 1,2-oxathiethane-2,2-dione; lactones such as β-propiolactone or γ-butyrolactone; and carbonate ester such as dimethyl carbonate, methyl ethyl carbonate, or diethyl carbonate. From the viewpoint of the achievement of both safety and reactivity, carbonate ester is preferable, and dimethyl carbonate is more preferable, as an alkylating agent.

As a complexation agent, known Lewis acid can be used. The term "Lewis acid" is used to mean "a substance having an empty orbit capable of receiving at least one electron pair, namely, an electron pair receptor." The definition of such Lewis acid is described in Gerry March, Advanced Organic Chemistry (reactions, mechanisms, and structure), $3^{rd}$ edition, Willy Interscience, pp. 227-234, for example. The aforementioned Lewis acid used in the present invention generally consists of a semimetallic compound, a metallic compound, or a complex thereof. Preferred examples of such Lewis acid may include boron fluoride and an ether complex thereof ($BF_3.Et_2O$, $BF_3$, $Me_2O$, $BF_3.THF$, etc.), titanium chloride, aluminum chloride, aluminum bromide, tin chloride, zinc chloride, zinc bromide, zinc iodide, zinc trifluoromethanesulfonate, zinc acetate, zinc nitrate, zinc tetrafluoroborate, manganese chloride, manganese bromide, nickel chloride, nickel bromide, nickel cyanide, nickel acetylacetonate, cadmium chloride, cadmium bromide, stannous chloride, stannous bromide, stannous sulfate, stannous tartrate, the chlorides, bromides, sulfates, nitrates, carboxylates, or trifluoromethanesulfonates of rare earth metal elements such as lanthanum, cerium, praseodymium, neodymium, samarium, europium, gadolinium, terbium, dysprosium, holmium, erbium, thulium, ytterbium and lutetium, cobalt chloride, ferrous chloride, and yttrium chloride. A mixture consisting of several types of Lewis acids can also be used. In addition, it is also possible to add Lewis acid to alkali chloride metal, and particularly to lithium chloride or sodium chloride, so as to stabilize Lewis acid in an aqueous solution, as necessary. The molar ratio between lithium chloride or sodium chloride and Lewis acid is within an extremely broad range. It is between 0 and 100, for example. Such a molar ratio can be adjusted to a specific ratio, depending on the stability of Lewis acid in water. Among others, boron fluoride and an ether complex thereof ($BF_3.Et_2O$, $BF_3$, $Me_2O$, $BF_3.THF$, etc.) are preferable.

As a diazotization agent, nitrous acid compounds such as sodium nitrite, potassium nitrite, isoamyl nitrite, ethyl nitrite, butyl nitrite, or propyl nitrite, and nitrosylsulfuric acid can be used. Preferably, sodium nitrite can be used.

In the present invention, a solvent used in an alkylation reaction may be either water or an organic solvent. In addition, a mixed solvent consisting of water and an organic solvent may also be used. Taking into consideration the intended use for a biosensor, a single use of water, or a mixed solvent consisting of water and an organic solvent capable of mixing with water, is preferable. Specific examples of an organic solvent capable of mixing with water that is preferably used herein may include methanol, ethanol, isopropyl alcohol, tetrahydrofuran, formamide, dimethylformamide, dimethyl sulfoxide, acetonitrile, ethylene glycol, and ethylene glycol dimethyl ether.

The biosensor of the present invention has as broad a meaning as possible, and the term biosensor is used herein to mean a sensor, which converts an interaction between biomolecules into a signal such as an electric signal, so as to measure or detect a target substance. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, or hormone/receptor. The biosensor operates on the principle that a substance having an affinity with another substance, as described above, is immobilized on a substrate to be used as a molecule-recognizing substance, so that the corresponding substance can be selectively measured.

The substrate of the biosensor of the present invention is preferably a metal surface or metal film. A metal constituting the metal surface or metal film is not particularly limited, as long as surface plasmon resonance is generated when the metal is used for a surface plasmon resonance biosensor. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, and particularly preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and have excellent workability are preferably used.

Preferably in the present invention, the substrate is a metal surface or a metal film which was coated with a hydrophobic polymer or a water-soluble polymer or a metal surface or a metal film which has a self-assembling monolayer. The hydrophobic polymer, the water-soluble polymer and the self-assembling monolayer are described below.

The hydrophobic polymer that can be used in the present invention is generally a polymer compound having no water-absorbing properties or having low water-absorbing properties. The solubility of such compound in water (25° C.) is preferably 10% or less, more preferably 1% or less, and most preferably 0.1% or less.

Specific examples of the hydrophobic polymer include a polyacrylic acid derivative, a polymethacrylic acid derivative, polyethylene (PE), polypropylene (PP), polybutadiene, polymethylpentene, cycloolefin polymer, polystyrene (PS), acrylonitrile/butadiene/styrene copolymer (ABS), styrene/maleic anhydride copolymer/polyvinyl chloride (PVC), polyethylene terephthalate (PET), polyethylene naphthalate (PEN), nylon 6, nylon 66, cellulose acetate (TAC), polycarbonate (PC), modified polyphenylene ether (m-PPE), polyphenylene sulfide (PPS), polyether ketone (PEK), polyether ether ketone (PEEK), polysulfone (PSF), polyether sulfone (PES), polyphenylene sulfide (PPS), and liquid crystal polymer (LCP). A physiologically active substance can be discriminated by charge of the substance on the two-dimensional surface, when a functional group which gives a charge is introduced on the surfaces of the above-mentioned hydrophobic polymer.

Coating of a substrate with a hydrophobic polymer can also be performed by a standard method such as spin coating, air knife coating, bar coating, blade coating, slide coating, and curtain coating methods, a spray method, a vacuum evaporation method, a cast method, and a dip method.

The coating thickness of a hydrophobic polymer is not particularly limited, but it is preferably between 0.1 nm and 500 nm, and particularly preferably between 1 nm and 300 nm.

Examples of the water-soluble polymer used in the present invention may include polyhydroxy polymers. Examples thereof may include polysaccharides (e.g. agarose, dextran, carrageenan, alginic acid, starch, and cellulose), and synthetic polymers (e.g. polyvinyl alcohol). In the present invention, polysaccharides are preferably used, and dextran is most preferable.

In the present invention, a polyhydroxy polymer having a mean molecular weight between 10,000 and 2,000,000 is preferably used. A polyhydroxy polymer having a mean molecular weight preferably between 20,000 and 2,000,000, more preferably between 30,000 and 1,000,000, and most preferably between 200,000 and 800,000, can be used.

For example, a polyhydroxy polymer is allowed to react with bromoacetic acid under basic conditions, so that it can be carboxylated. By controlling reaction conditions, a certain ratio of hydroxy groups contained in a polyhydroxy compound at an initial stage can be carboxylated. In the present invention, 1% to 90% hydroxy groups can be carboxylated, for example. The carboxylation rate of a surface coated with any given polyhydroxy polymer can be calculated by the following method. Using a di-tert-butylcarbodiimide/pyridine catalyst, the surface of a film is subjected to gas phase modification with trifluoroethanol at 50° C. for 16 hours. Thereafter, the amount of fluorine derived from trifluoroethanol is measured by ESCA (electron spectroscopy for chemical analysis), and the ratio between the amount of fluorine and the amount of oxygen on the film surface (hereinafter referred to as F/O value) is calculated. A theoretical F/O value obtained when all hydroxy groups have been carboxylated is set at 100%. Then, a F/O value obtained by carboxylation under certain conditions is measured. Thus, a carboxylation rate at that time can be calculated.

A polyhydroxy polymer can be attached to a metal film via an organic molecule $X^1$—$R^1$—$Y^1$. Such an organic molecule $X^1$—$R^1$—$Y^1$ will be described in detail.

$X^1$ is a group having ability to bind to a metal film. Specifically, asymmetrical or symmetrical sulfide (—$SSR^{11}Y^{11}$, —$SSR^1Y^1$), sulfide (—$SR^{11}Y^{11}$, —$SR^1Y^1$), diselenide (—$SeSeR^{11}Y^{11}$, —$SeSeR^1Y^1$), selenide (—$SeR^{11}Y^{11}$, —$SeR^1Y^1$), thiol (—SH), nitrile (—CN), isonitrile, nitro (—$NO_2$), selenol (—SeH), a trivalent phosphorus compound, isothiocyanate, xanthate, thiocarbamate, phosphine, thioacid, and dithioacid (—COSH, —CSSH) are preferably used.

$R^1$ (and $R^{11}$) are discontinued by hetero atoms in some cases. For a moderately dense load, these are preferably straight chains (that are not branched), and these are hydrocarbon chains containing double and/or triple bonds in some cases. Such a chain preferably has a length consisting of more than 10 atoms. A carbon chain may be perfluorinated in some cases.

$Y^1$ and $Y^{11}$ are groups for binding with a polyhydroxy polymer. $Y^1$ and $Y^{11}$ are preferably identical and have properties of capable of binding to a polyhydroxy polymer directly or after activation. Specifically, a hydroxyl, carboxyl, amino, aldehyde, hydrazide, carbonyl, epoxy, or vinyl group can be used.

Specific examples of an organic molecule $X^1$—$R^1$—$Y^1$ used herein may include 10-carboxy-1-decanethiol, 4,4'-dithiodibutyric acid, 11-hydroxy-1-undecanethiol, and 11-amino-1-undecanethiol.

The self-assembling monolayer is described below. A sulfur compound such as thiol or disulfide spontaneously adsorbs on a precious metal substrate such as gold, so as to provide an ultra-thin membrane with a size of a single molecule. In addition, since an aggregate thereof has a sequence that depends on the crystal lattice of a substrate or the molecular structure of an admolecule, it is called a self assembled monolayer. Examples of the self-assembled monolayer may include alkanethiols on gold surface, alkylsilanes on glass surface, and alcohols on silicon surface. Examples of alkanethiols may include 7-carboxy-1-heptanethiol, 10-carboxy-1-decanethiol, 4,4'-dithiodibutyric acid, 11-hydroxy-1-undecanethiol, 11-amino-1-undecanethiol, or the like.

A biosensor which comprises a substrate coated with a hydrophobic polymer or a water-soluble polymer or a substrate having a self-assembling monolayer, preferably has a —COOH group as a functional group capable of immobilizing a physiologically active substance on the outermost surface of the substrate. A hydrophobic organic layer having a —COOH group can be produced by the production methods described in JP Patent Publication (Kokai) No. 2004-286539, Japanese Patent Application No. 2004-238396, etc. A hydrophilic organic layer having a —COOH group can be produced by the production method described in Japanese Patent No. 2815120.

A phenol compound having a substituent whose electron-withdrawing ability is increased as a result of a chemical reaction is allowed to react with the aforementioned substrate having a —COOH group, so as to produce a substrate modified with a phenyl ester group having a substituent whose electron-withdrawing ability is increased as a result of a chemical reaction.

Subsequently, on the surface of the thus obtained substrate, the phenyl ester group having a substituent whose electron-withdrawing ability is increased as a result of a chemical reaction is activated by a chemical reaction, and thereafter, the activated phenyl ester group is allowed to react with a compound having an amino group, so as to immobilize a physiologically active substance on a metal surface or a metal film.

A physiologically active substance immobilized on the surface for the biosensor of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

When a physiologically active substance is a protein such as an antibody or enzyme or nucleic acid, an amino group, thiol group or the like of the physiologically active substance is covalently bound to a functional group located on a metal surface, so that the physiologically active substance can be immobilized on the metal surface.

A biosensor to which a physiologically active substance is immobilized as described above can be used to detect and/or measure a substance which interacts with the physiologically active substance.

Thus, the present invention provides a method of detecting and/or measuring a substance interacting with the physiologically active substance immobilized to the biosensor of the present invention, to which a physiologically active substance is immobilized, wherein the biosensor is contacted with a test substance.

As such a test substance, for example, a sample containing the above substance interacting with the physiologically active substance can be used.

In the present invention, it is preferable to detect and/or measure an interaction between a physiologically active substance immobilized on the surface used for a biosensor and a test substance by a nonelectric chemical method. Examples of a non-electrochemical method may include a surface plasmon resonance (SPR) measurement technique, a quartz crystal microbalance (QCM) measurement technique, and a measurement technique that uses functional surfaces ranging from gold colloid particles to ultra-fine particles.

In a preferred embodiment of the present invention, the biosensor of the present invention can be used as a biosensor for surface plasmon resonance which is characterized in that it comprises a metal film placed on a transparent substrate.

A biosensor for surface plasmon resonance is a biosensor used for a surface plasmon resonance biosensor, meaning a member comprising a portion for transmitting and reflecting light emitted from the sensor and a portion for immobilizing a physiologically active substance. It may be fixed to the main body of the sensor or may be detachable.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

A device using a system known as the Kretschmann configuration is an example of a surface plasmon measurement device for analyzing the properties of a substance to be measured using a phenomenon whereby a surface plasmon is excited with a lightwave (for example, Japanese Patent Laid-Open No. 6-167443). The surface plasmon measurement device using the above system basically comprises a dielectric block formed in a prism state, a metal film that is formed on a face of the dielectric block and comes into contact with a measured substance such as a sample solution, a light source for generating a light beam, an optical system for allowing the above light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the above interface.

In order to achieve various incident angles as described above, a relatively thin light beam may be caused to enter the above interface while changing an incident angle. Otherwise, a relatively thick light beam may be caused to enter the above interface in a state of convergent light or divergent light, so that the light beam contains components that have entered therein at various angles. In the former case, the light beam whose reflection angle changes depending on the change of the incident angle of the entered light beam can be detected with a small photodetector moving in synchronization with the change of the above reflection angle, or it can also be detected with an area sensor extending along the direction in which the reflection angle is changed. In the latter case, the light beam can be detected with an area sensor extending to a direction capable of receiving all the light beams reflected at various reflection angles.

With regard to a surface plasmon measurement device with the above structure, if a light beam is allowed to enter the metal film at a specific incident angle greater than or equal to a total reflection angle, then an evanescent wave having an electric distribution appears in a measured substance that is in contact with the metal film, and a surface plasmon is excited by this evanescent wave at the interface between the metal film and the measured substance. When the wave vector of the evanescent light is the same as that of a surface plasmon and thus their wave numbers match, they are in a resonance state, and light energy transfers to the surface plasmon. Accordingly, the intensity of totally reflected light is sharply decreased at the interface between the dielectric block and the metal film. This decrease in light intensity is generally detected as a dark line by the above light-detecting means. The above resonance takes place only when the incident beam is p-polarized light. Accordingly, it is necessary to set the light beam in advance such that it enters as p-polarized light.

If the wave number of a surface plasmon is determined from an incident angle causing the attenuated total reflection (ATR), that is, an attenuated total reflection angle (θSP), the dielectric constant of a measured substance can be determined. As described in Japanese Patent Laid-Open No. 11-326194, a light-detecting means in the form of an array is considered to be used for the above type of surface plasmon measurement device in order to measure the attenuated total reflection angle (θSP) with high precision and in a large dynamic range. This light-detecting means comprises multiple photo acceptance units that are arranged in a certain direction, that is, a direction in which different photo acceptance units receive the components of light beams that are totally reflected at various reflection angles at the above interface.

In the above case, there is established a differentiating means for differentiating a photodetection signal outputted from each photo acceptance unit in the above array-form light-detecting means with regard to the direction in which the photo acceptance unit is arranged. An attenuated total reflection angle (θSP) is then specified based on the derivative value outputted from the differentiating means, so that properties associated with the refractive index of a measured substance are determined in many cases.

In addition, a leaking mode measurement device described in "Bunko Kenkyu (Spectral Studies)" Vol. 47, No. 1 (1998), pp. 21 to 23 and 26 to 27 has also been known as an example of measurement devices similar to the above-described device using attenuated total reflection (ATR). This leaking mode measurement device basically comprises a dielectric block formed in a prism state, a clad layer that is formed on a face of the dielectric block, a light wave guide layer that is formed on the clad layer and comes into contact with a sample solution, a light source for generating a light beam, an optical system for allowing the above light beam to enter the dielectric block at various angles so that total reflection conditions can be obtained at the interface between the dielectric block and the clad layer, and a light-detecting means for detecting the excitation state of waveguide mode, that is, the state of attenuated total reflection, by measuring the intensity of the light beam totally reflected at the above interface.

In the leaking mode measurement device with the above structure, if a light beam is caused to enter the clad layer via the dielectric block at an incident angle greater than or equal to a total reflection angle, only light having a specific wave number that has entered at a specific incident angle is transmitted in a waveguide mode into the light wave guide layer, after the light beam has penetrated the clad layer. Thus, when the waveguide mode is excited, almost all forms of incident light are taken into the light wave guide layer, and thereby the state of attenuated total reflection occurs, in which the intensity of the totally reflected light is sharply decreased at the above interface. Since the wave number of a waveguide light depends on the refractive index of a measured substance placed on the light wave guide layer, the refractive index of the measurement substance or the properties of the measured substance associated therewith can be analyzed by determining the above specific incident angle causing the attenuated total reflection.

In this leaking mode measurement device also, the above-described array-form light-detecting means can be used to detect the position of a dark line generated in a reflected light due to attenuated total reflection. In addition, the above-described differentiating means can also be applied in combination with the above means.

The above-described surface plasmon measurement device or leaking mode measurement device may be used in random screening to discover a specific substance binding to a desired sensing substance in the field of research for development of new drugs or the like. In this case, a sensing substance is immobilized as the above-described measured substance on the above thin film layer (which is a metal film in the case of a surface plasmon measurement device, and is a clad layer and a light guide wave layer in the case of a leaking mode measurement device), and a sample solution obtained by dissolving various types of test substance in a solvent is added to the sensing substance. Thereafter, the above-described attenuated total reflection angle (θSP) is measured periodically when a certain period of time has elapsed.

If the test substance contained in the sample solution is bound to the sensing substance, the refractive index of the sensing substance is changed by this binding over time. Accordingly, the above attenuated total reflection angle (θSP) is measured periodically after the elapse of a certain time, and it is determined whether or not a change has occurred in the above attenuated total reflection angle (θSP), so that a binding state between the test substance and the sensing substance is measured. Based on the results, it can be determined whether or not the test substance is a specific substance binding to the sensing substance. Examples of such a combination between a specific substance and a sensing substance may include an antigen and an antibody, and an antibody and an antibody. More specifically, a rabbit anti-human IgG antibody is immobilized as a sensing substance on the surface of a thin film layer, and a human IgG antibody is used as a specific substance.

It is to be noted that in order to measure a binding state between a test substance and a sensing substance, it is not always necessary to detect the angle itself of an attenuated total reflection angle (θSP). For example, a sample solution may be added to a sensing substance, and the amount of an attenuated total reflection angle (θSP) changed thereby may be measured, so that the binding state can be measured based on the magnitude by which the angle has changed. When the above-described array-form light-detecting means and differentiating means are applied to a measurement device using attenuated total reflection, the amount by which a derivative value has changed reflects the amount by which the attenuated total reflection angle (θSP) has changed. Accordingly, based on the amount by which the derivative value has changed, a binding state between a sensing substance and a test substance can be measured (Japanese Patent Application No. 2000-398309 filed by the present applicant). In a measuring method and a measurement device using such attenuated total reflection, a sample solution consisting of a solvent and a test substance is added dropwise to a cup- or petri dish-shaped measurement chip wherein a sensing substance is immobilized on a thin film layer previously formed at the bottom, and then, the above-described amount by which an attenuated total reflection angle (θSP) has changed is measured.

Moreover, Japanese Patent Laid-Open No. 2001-330560 describes a measurement device using attenuated total reflection, which involves successively measuring multiple measurement chips mounted on a turntable or the like, so as to measure many samples in a short time.

When the biosensor of the present invention is used in surface plasmon resonance analysis, it can be applied as a part of various surface plasmon measurement devices described above.

The present invention will be further specifically described in the following examples. However, the examples are not intended to limit the scope of the present invention.

EXAMPLES

Example 1

The present example shows that the alkylated form (quaternized form) of an m-N,N-dimethylaminophenyl ester is more excellent than the m-N,N-dimethylaminophenyl ester in terms of ability to bind to a physiologically active substance. Using a protein (CA: carbonic anhydrase) labeled with fluorescent dye Cy5, an experiment was conducted.

(Production of Sensor Chip)

The sensor chip of the present invention was produced by the following method.

(1) Formation of Gold Film on Plastic Prism

A thin gold film was formed on the upper surface of a plastic prism obtained by the injection molding of ZEONEX (manufactured by ZEON Corporation) by the following method.

(1-1) Formation of Gold Film

The prism was attached to the substrate holder of a sputter device. After decompression (base pressure: $1\times10^3$ Pa or less), Ar gas (1 Pa) was introduced therein. Thereafter, while rotating the substrate holder (20 rpm), RF power (0.5 kW) was applied to the substrate holder for approximately 9 minutes, so as to subject the surface of the prism to a plasma treatment. Subsequently, introduction of Ar gas was terminated, followed by decompression. Thereafter, Ar gas was introduced again (0.5 Pa), and while rotating the substrate holder (10 to 40 rpm), DC power (0.2 kW) was applied to a Cr target having a size of 8 inch for approximately 30 seconds, so as to form a thin Cr film having a thickness of 2 nm. Subsequently, introduction of Ar gas was terminated, followed by decompression again. Thereafter, Ar gas was introduced again (0.5 Pa), and while rotating the substrate holder (20 rpm), DC power (1 kW) was applied to an Au target having a size of 8 inch for approximately 50 seconds, so as to form a thin Au film having a thickness of approximately 50 nm. The obtained sample was called chip A.

(2) Coating of Polymer

A thin polymer film was formed on the thin gold film of chip A by the following method.

(2-1) Preparation of Polymer Solution A 1.5 g of polymer (F-1) was dissolved in 100 ml of anhydrous MiBK (methyl isobutyl ketone), and the obtained solution was then filtrated with a microfilter having a pore diameter of 0.45 μm. The water content of the anhydrous MiBK was 20 ppm.

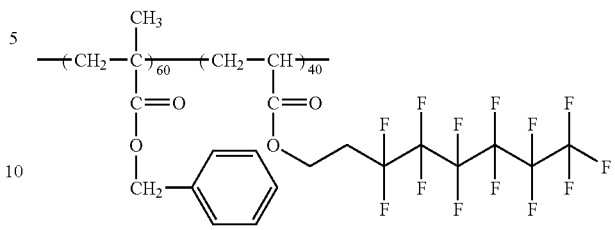

F-1

(2-2) Spin-coating

Chip A was set to a spin-coater (SC-408S sample hermetically sealed spin-coater; manufactured by Oshikane). Chip A was fixed at the position that was 135 mm from the center of the spin-coater. 200 μl of polymer solution A was casted on chip A, such that the entire gold film could be coated with the solution. Thereafter, a windbreak cover was set, such that chip A could be completely coated therewith. Thereafter, the chip was spun at 200 rpm for 60 seconds. After termination of the rotation, the chip was left at rest for 5 minutes.

(2-3) Vacuum Drying

Chip A, which had been spin-coated with the polymer, was subjected to vacuum drying for 16 hours. The obtained sample was called chip B.

(3) Hydrolysis of Polymer Surface

The surface of the thin polymer film of chip B was hydrolyzed by the following method, so as to generate a COOH group on the outermost surface.

(3-1) Hydrolysis

Chip B was immersed in 1 N NaOH solution, and it was then conserved in a thermostatic bath at 60° C. for 16 hours.

(3-2) Washing

The chip was removed from the 60° C. thermostatic bath, and it was subjected to natural cooling for 15 minutes. Thereafter, the chip was washed with ultra pure water. The obtained sample was called chip C.

(4) Binding of 5-aminovaleric acid 5-aminovaleric acid was allowed to covalently bind to the COOH group existing on the surface of chip C by the following method.

(4-1) Preparation of Activator Solution and 5-aminovaleric acid Solution 0.1 M NHS solution: 1.16 g of NHS (N-hydroxysulfosuccinimide) was dissolved in ultrapure water, so as to prepare 100 mL of the above solution.

0.4 M EDC solution: 7.7 g of EDC (1-ethyl-3-[3-dimethylaminopropyl]carbodiimide hydrochloride) was dissolved in ultrapure water, so as to prepare 100 mL of the above solution.

1 M 5-aminovaleric acid solution: 11.7 g of 5-aminovaleric acid was dissolved in 80 mL of ultrapure water, and the pH of the solution was then adjusted to pH 8.5 by addition of 1 N NaOH. Thereafter, ultrapure water was further added thereto, so as to prepare 100 mL of the above solution.

(4-2) Activation

Chip C was drained using an air gun. Chip C was set in a wet box (a tight box in which a wet cloth had been placed at the bottom, wherein the humidity was maintained at 90% RH or more in a hermetically sealed state). Thereafter, 200 μl of a mixed solution consisting of 100 μl of the 0.1 M NHS solution and 100 μl of the 0.4 M EDC solution was casted thereon. Thereafter, a PET film with a size of 120 mm×8.5 mm and with a thickness of 175 μm was placed thereon, so as to cover the surface while spreading the solution. During this reaction, the ratio of the surface area of the solution, which was not allowed to come into contact with air, to the surface area of the solution, which was allowed to come into contact with air, was 26. The wet box was hermetically sealed, and it was then left at rest at 25° C. for 60 minutes.

(4-3) Washing

The PET film was removed from the sample taken out of the wet box, and the sample was then washed with ultrapure water. The obtained sample was called chip D.

(4-4) 5-aminovaleric acid Reaction

A 5-aminovaleric acid reaction was initiated within 1 hour after completion of the activation reaction. First, chip D was drained using an air gun. Chip D was set in a wet box, and 200 μof a 1 M 5-aminovaleric acid solution was then casted thereon. Thereafter, a PET film with a size of 120 mm×8.5 mm and with a thickness of 175 μm was placed thereon, so as to cover the surface while spreading the solution. During this reaction, the ratio of the surface area of the solution, which was not allowed to come into contact with air, to the surface area of the solution, which was allowed to come into contact with air, was 24. The wet box was hermetically sealed, and it was then left at rest at 25° C. for 90 minutes.

(4-5) Washing

The PET film was removed from the sample taken out of the wet box, and the sample was then washed with ultrapure water. The obtained sample was called chip E.

(5-1) Preparation of Reaction Solutions 0.1 M NHS solution: 1.16 g of NHS was dissolved in ultrapure water, so as to prepare 100 mL of the above solution.

0.1 M m-DMAP solution: 1.37 g of m-DMAP (m-N,N-dimethylaminophenol) was dissolved in ultrapure water, so as to prepare 100 mL of the above solution.

0.4 M EDC solution: 7.7 g of EDC was dissolved in ultrapure water, so as to prepare 100 mL of the above solution.

(5-2) Formation of NHS Ester

Chip E was drained using an air gun, and it was then immobilized on the seating of a dispenser manufactured by Musashi Engineering, Inc. Subsequently, a mixed solution consisting of 2 mL of the 0.1M NHS solution and 2 mL of the 0.4M EDC solution was poured into a syringe. 15 μL each of the above mixed solution was spotted on 8 points of chip E at intervals of 18 mm. The diameter of a droplet was approximately 3.5 mm. After such spotting, chip E was placed in a wet box, and the wet box was then hermetically sealed. It was left at rest at 25° C. for 60 minutes. The obtained sample was called chip F.

(5-3) Formation of m-DMAP Ester

Chip E was drained using an air gun, and it was then immobilized on the seating of a dispenser manufactured by Musashi Engineering, Inc. Subsequently, a mixed solution consisting of 2 mL of the 0.1M m-DMAP solution and 2 mL of the 0.4M EDC solution was poured into a syringe. 15 μL each of the above mixed solution was spotted on 8 points of chip E at intervals of 18 mm. The diameter of a droplet was approximately 3.5 mm. After such spotting, chip E was placed in a wet box, and the wet box was then hermetically sealed. It was left at rest at 25° C. for 60 minutes. The obtained sample was called chip G.

(5-4) Methylation of m-DMAP Ester

An m-DMAP ester was formed by the aforementioned operations. The chip surface was washed with ultrapure water, and 8 μL each of a mixed solution consisting of 1.0 ml of dimethyl sulfate, 4.0 ml of ultrapure water, and 5.0 ml of ethanol was spotted on 8 points of chip E at intervals of 18 mm. The diameter of a droplet was approximately 3.5 mm. After such spotting, chip E was placed in a wet box, and the wet box was then hermetically sealed. It was left at rest at 25° C. for 60 minutes. The obtained sample was called chip H.

(Immobilization of Fluorescent Protein)

(6-1) Synthesis of Cy5-introduced CA

Cy5 Mono-reactive Dye Pack (Amersham) was purchased. In accordance with standard protocols included therewith, CA (carbonic anhydrase: Sigma) was reacted with a Cy5 NHS ester, and the reaction product was then purified, so as to obtain Cy5-introduced CA. It was confirmed that 4.7 molecules of Cy5 were introduced into a one molecule of CA.

(6-2) Preparation of Cy5-introduced CA Solution

A Cy5-introduced CA solution was prepared using a certain buffer solution, resulting in 50 μg/ml Cy5-introduced CA contained therein. Regarding pH, pH 4.0 was adjusted with an acetate buffer, pH 7.4 was adjusted with an HBS-N buffer, pH 8.5 was adjusted with a borate buffer, and pH 9.4 was adjusted with a carbonate buffer.

(6-3) Immobilization of Cy5-introduced CA Solution

Cy5-introduced CA with a certain pH was spotted on the esterified portions of chips F, G, and H. The diameter of a droplet was set at approximately 3.5 mm. The thus spotted chip E was placed in a wet box, and the wet box was then hermetically sealed. It was left at rest at 25° C. for 60 minutes.

(Measurement of Fluorescence Intensity)

Using Fluoro Image Analyzer (FLA8000; manufactured by Fuji Photo Film Co., Ltd.), the relative value of the fluorescence intensity on the surface of each of the aforementioned sensor chips was compared with one another (excitation wavelength: 635 nm; measurement wavelength: 675 nm). Since fluorescence is observed on the surface of each sensor chip only when the ester on the surface of the sensor chip is reacted with Cy5-introduced CA, the present method can be an effective means for evaluating the activation ability of the ester. The obtained results are shown in Table 2.

TABLE 2

| | Amount of fluorescent protein binding to various types of esters | | | | |
|---|---|---|---|---|---|
| | Fluorescent intensity (relative value) | pH 4.0 | pH 7.4 | pH 8.5 | pH 9.4 | Remarks |
| 1 | NHS ester | 80,000 | 20,000 | 20,000 | 18,000 | Comparative example |
| 2 | m-DMAPh ester | 40,000 | 5,000 | 100 | 100 | Comparative example |
| 3 | m-DMAPh ester + dimethyl sulfate | 120,000 | 60,000 | 60,000 | 40,000 | The present invention |

An increase in fluorescence intensity due to quaternization, namely, an increase in the binding amount of Cy5-introduced CA, was confirmed in all the measured pH regions. In particular, in a pH range of 7.4 or greater, almost no Cy5-introduced CA bound to a non-quaternized portion, whereas Cy5-introduced CA bound to a quaternized portion. This degree was confirmed to be equivalent to that of an NHS ester. From these results, it was proved that the quaternized form of m-N,N-dimethylaminophenyl ester is more excellent than the m-N,N-dimethylaminophenyl ester in terms of ability of binding to a physiologically active substance.

EFFECTS OF THE INVENTION

In the biosensor of the present invention, a functional group used for binding a physiologically active substance can be conserved in the form of an inactive ester, and it can be converted to an activated ester by simple operations immediately before formation of an amide bond.

The invention claimed is:

1. A biosensor which comprises a substrate that has been modified with a phenyl ester group having a dialkylamino substituent group whose electron-withdrawing ability is increased as a result of a chemical reaction.

2. The biosensor according to claim 1 wherein the substrate is a metal surface or a metal film which consists of a free electron metal selected from the group consisting of gold, silver, copper, platinum, and aluminum.

3. The biosensor according to claim 1 which is used in non-electrochemical detection.

4. The biosensor according to claim 1 which is used in surface plasmon resonance analysis.

5. A method for immobilizing a compound having an amino group on a substrate, which comprises: activating a phenyl ester group existing on the substrate, by performing a chemical reaction which increases the electron-withdrawing ability of a dialkylamino substituent group of the phenyl ester; and then reacting the activated phenyl ester group with the compound having an amino group.

6. The method according to claim 5, wherein the chemical reaction is an alkylation reaction, a complexation reaction, or a diazotization reaction.

7. The method according to claim 5, wherein the compound having an amino group is a physiologically active substance.

8. The biosensor according to claim 1 on which a compound having an amino group is immobilized by a method of mobilizing a compound having an amino group on a substrate, which comprises: activating a phenyl ester group existing on the substrate, by performing a chemical reaction which increases the electron-withdrawing ability of a dialkylamino substituent group of the phenyl ester; and then reacting the activated phenyl ester group with the compound having an amino group.

9. A method for detecting of measuring a substance interacting with a physiologically active substance, which comprises a step of contacting the biosensor of claim 1, to which a physiologically active substance having an amino group is bound, with a test substance; and a step of detecting or measuring the substance interacting with the physiologically active substance.

10. The method according to claim 9, wherein a substance interacting with the compound having an amino group is detected or measured by a non-electrochemical method.

11. The method according to claim 9, wherein a substance interacting with the compound having an amino group is detected or measured by surface plasmon resonance analysis.

* * * * *